(12) United States Patent
Chang

(10) Patent No.: US 7,029,433 B2
(45) Date of Patent: Apr. 18, 2006

(54) DEVICE FOR CARDIAC RESTORATION

(76) Inventor: Sheldon S. Chang, P.O. Box 273, Port Jefferson, NY (US) 11777-0273

( * ) Notice: Subject to any disclaimer, the term of this patent is extended or adjusted under 35 U.S.C. 154(b) by 0 days.

(21) Appl. No.: 10/099,822

(22) Filed: Mar. 16, 2002

(65) Prior Publication Data

US 2003/0187481 A1    Oct. 2, 2003

(51) Int. Cl.
*A61N 1/362* (2006.01)
(52) U.S. Cl. ............................................. 600/17
(58) Field of Classification Search ............. 600/16–18
See application file for complete search history.

(56) References Cited

U.S. PATENT DOCUMENTS

| | | | | | |
|---|---|---|---|---|---|
| 3,911,898 | A | * | 10/1975 | Leachman, Jr. | 600/17 |
| 4,955,856 | A | * | 9/1990 | Phillips | 600/16 |
| 4,995,857 | A | * | 2/1991 | Arnold | 600/16 |
| 5,069,680 | A | * | 12/1991 | Grandjean | 623/3.12 |
| 5,112,349 | A | * | 5/1992 | Summers et al. | 623/3.15 |
| 5,318,592 | A | * | 6/1994 | Schaldach | 607/5 |
| 5,722,930 | A | * | 3/1998 | Larson et al. | 600/16 |
| 5,848,962 | A | * | 12/1998 | Feindt et al. | 600/16 |
| 5,904,646 | A | * | 5/1999 | Jarvik | 600/16 |
| 6,132,363 | A | * | 10/2000 | Freed et al. | 600/16 |
| 6,146,325 | A | * | 11/2000 | Lewis et al. | 600/16 |
| 6,254,525 | B1 | * | 7/2001 | Reinhardt et al. | 600/17 |
| 6,530,876 | B1 | * | 3/2003 | Spence | 600/16 |
| 6,585,635 | B1 | * | 7/2003 | Aldrich | 600/16 |

* cited by examiner

Primary Examiner—Jeffrey R. Jastrzab
(74) Attorney, Agent, or Firm—Hoffmann & Baron, LLP

(57) ABSTRACT

The invention herein is an enhanced VAD device (EVAD), for a physician to use to restore a dysfunctioning native heart with severe muscular damages to good health, so that the EVAD can be explanted eventually. The EVAD device comprises one or two VAD(s) a pacemaker for sending electrical pulses to the native heart, a first monitor for monitoring the patient's response to each of said electrical pulses from the pacemaker, controlled means a set of attachments for measuring biological and or clinical signals at various organs both inside and outside the patient's body, and a controller for facilitating the physician's work.

17 Claims, 4 Drawing Sheets

DEVICE FOR CARDIAC RESTORATION

BACKGROUND OF THE INVENTION

Heart failure remains a leading cause of disability and mortality in the United States and other Western nations. Heart failure progressing to end-stage cardiomyopathy can develop among patients with ischemic heart disease secondary to significant coronary atherosclerosis. Patients with viral myocarditis or valvular disease also are at risk for developing significant cardiomyopathy. Cardiac transplantation, ultimately, is the therapy for end-stage cardiomyopathy, whether the etiology is ischemic or non-ischemic, if pharmacologic measures fail. Transplantation however is limited by the available supply of donor organs. Consequently, efforts have been directed towards developing safe, implantable and long-term means of mechanical support for the patient awaiting transplantation. FDA approval has been granted to several mechanical ventricular assist devices (VADs) with application as a "bridge-to-transplant." Clinical studies demonstrate that implantation of such a device provides sufficient circulatory support to aid the patient's recovery from sequelae of end-stage cardiomyopathy such as renal and hepatic failure, and to allow physiologic rehabilitation until a donor heart is available. Cardiac arrhythmia is a significant complication of end-stage cardiomyopathy, with patients prone to developing either atrial fibrillation, resulting in an irregular rhythm with increased potential for stroke, or potentially fatal ventricular tachyarrythmias such as ventricular tachycardia or fibrillation. Cardiomyopathy patients can also develop bradyarrhythmia, or an abnormally slow heart rate. Treatment of these conduction disorders can require implantation of a permanent pacemaker, an automatic internal cardiac defibrillator or both.

As the clinical experience with implantable VADs has increased several investigators have observed a number of chronic heart failure patients who demonstrate not only recovery of end-organ damage and functional improvement, but also recovery of myocardial function following VAD implantation. These patients demonstrated recovery by several clinical parameters of myocardial function, including improved myocardial contractility or wall motion seen on serial echocardiography, increased exercise capacity greater than that expected from mechanical support alone, and the ability to maintain adequate cardiac output during periods of temporarily decreased VAD support. Only a few such patients have undergone VAD explantation and maintained native heart function sufficient to sustain life. However, it appears that long-term implantable mechanical ventricular assist devices can be applied in select patients not as a "bridge-to-transplant," but as a "bridge-to-recovery."

The present invention aims at providing a physician with means for natural heart restoration. In other words, to enlarge the class of patients for whom VAD explantation is to be made possible. Furthermore among this enlarged class, it is expected that after explantation, some patients will do far better than barely sustaining life, but will gradually be able to engage in normal activities with a completely restored native heart. In the present application, the terms "natural heart" and "native heart" mean one and the same heart of the patient.

BRIEF SUMMARY OF THE INVENTION

The invention herein is an enhanced VAD device (EVAD), for a physician to use to restore a dysfunctioning native heart with severe muscular damages to good health, so that the EVAD can be removed (explanted) eventually. The EVAD device comprises a VAD, a controlled means for sending electrical pulses to the native heart, a graphical means for monitoring the patient's response to each of said electrical pulses from the controlled means, a set of attachments for measuring biological and or clinical signals at various organs both inside and outside the patient's body, and electronic means for the convenience of the physician.

In our preferred embodiment, a "Linear Flow Blood Pump" (LFBP) is to be used as the said VAD device. [1] (Please see our list of references at the end of this application.)

There are two reasons why we prefer to use LFBP:
1. LFBP has least likelihood of complications, such as thrombus.
2. LFBP gives a few valuable means at the physician disposal in caring for his patient, such as independently and timely controlled pressure pulses and blood flow volume.

One or two LFBP can be used, depending on the patient's condition.

The controlled means for sending electrical pulses to the native heart is a radio signal controlled artificial pace-maker (AP) with its pulse rate and intensity controllable by the radio signal.

DETAILED DESCRIPTION OF THE INVENTION

Figure 1:
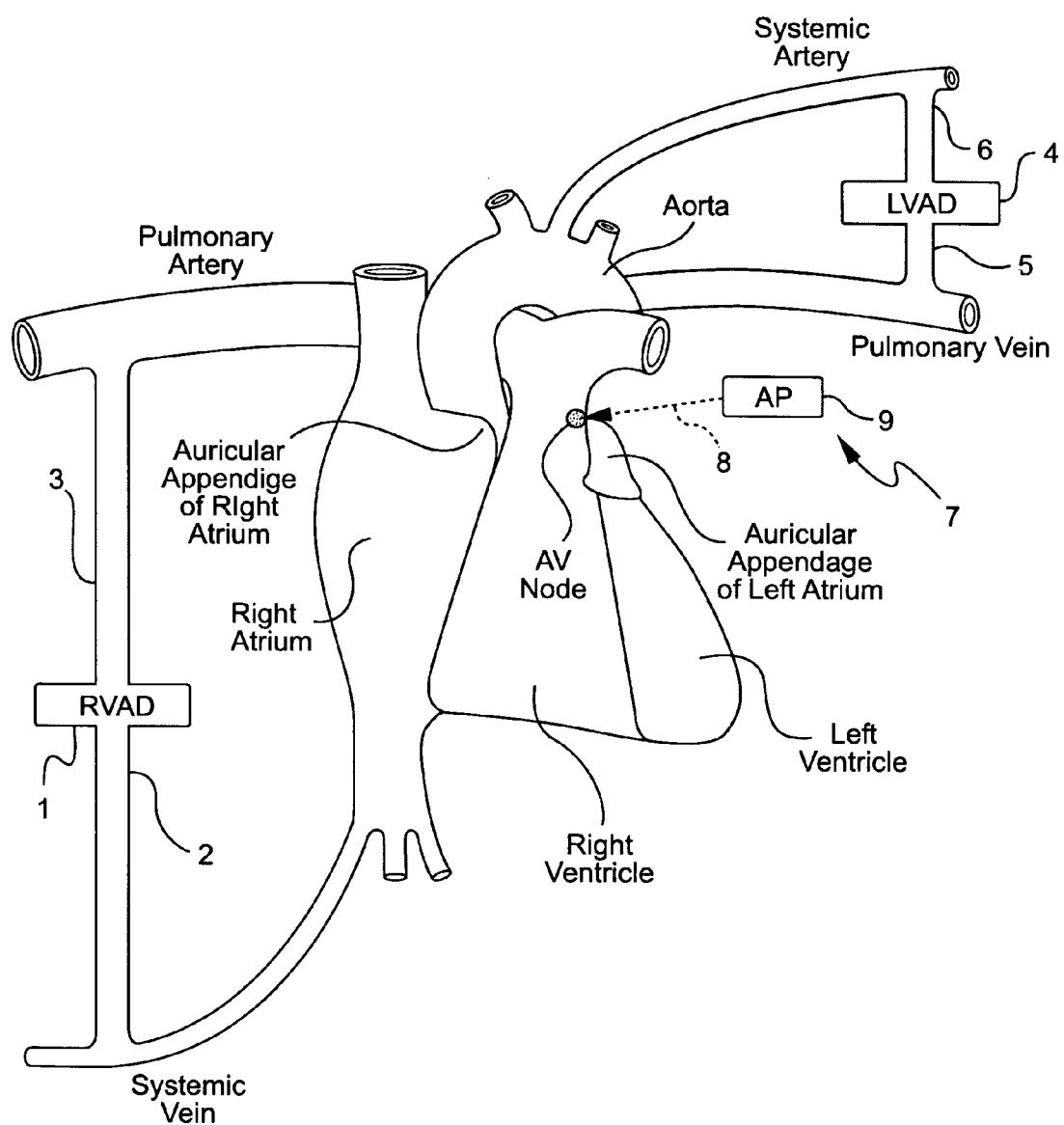
FIG. 1. shows the connections of an artificial pacemaker, and two VAD devices inside the patient's thorax.

As shown in FIG. 1, the right ventricular assist device [RVAD] 1 taps into a systemic vein for its input 2 and its output 3 taps into a pulmonary artery. The left ventricular assist device [LVAD] 4 taps into a pulmonary vein for its input 5 and its output 6 taps into a systemic artery. Both ventricular assist devices operate in parallel with their respective ventricles, and both tap into blood vessels for their inputs and outputs. The heart itself is never tapped. Because our aim is to restore the natural heart to good health. It is preferable not to do any damage to the natural heart.

The output electrical pulses 8 from the artificial pacemaker 7 is applied to the AV Node of the heart. Since the electrical wiring which is specially designed for transmitting such pulses, is very soft and flexible, it moves with the heart freely. The pulse rate and intensity of 8 are controlled by signal 9 which is issued either by the physician or by an AUTOPRO.

Figure 2:
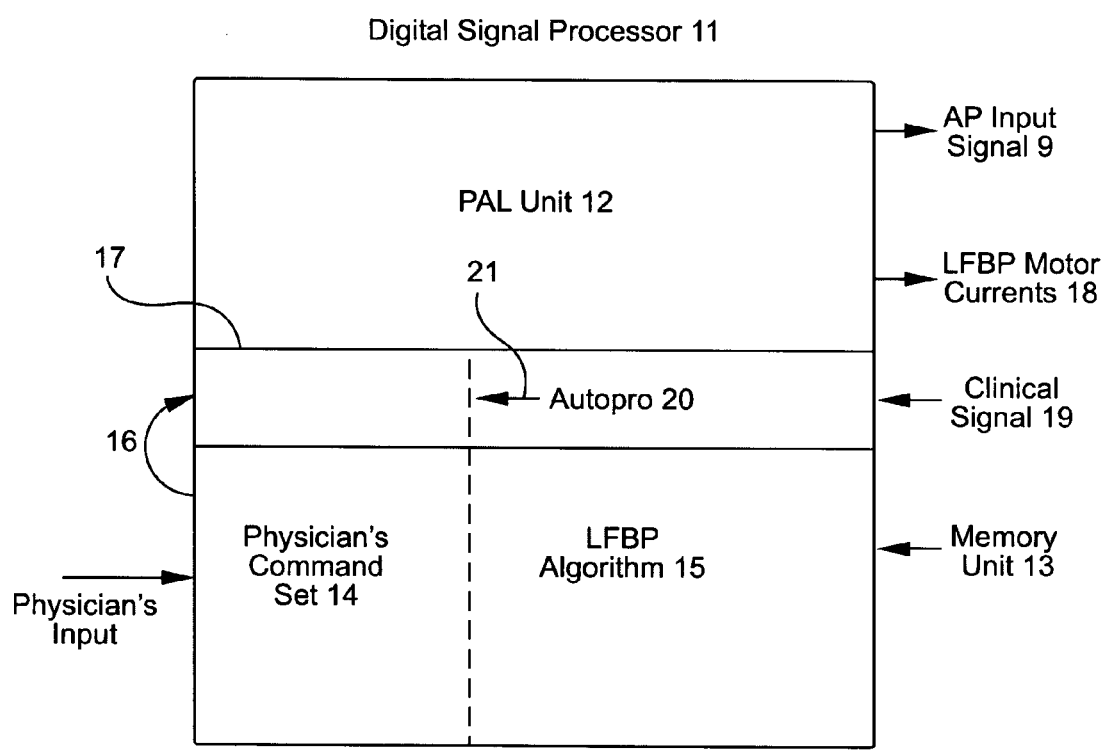
FIG. 2. illustrates an instruction set converter. (ISC)

The electronic means for the convenience of the physician is realized in FIG. 2. As shown in FIG. 2, the instruction set converter aims at isolating the physician from doing mechanical routine work.

In our preferred embodiment, LFBPs are used for each VAD. One reason is that the LFBP output blood pressure and flow volume can be independently controlled by using the following LFBP Algorithm:

"A pressure pulse in the direction of flow is generated by a sudden increase in the magnitude of the motor currents followed by a relatively gradual increase in the frequency of the motor currents. A pressure pulse against the direction of flow is generated by a sudden decrease in the magnitude of the motor currents followed by a relatively gradual decrease in the frequency of the motor currents. The 'relatively gradual' increase and decrease in frequency are in controlled amounts which are still quite fast. A gradual change in flow without pressure pulse is generated by a very slow and gradual change in the frequency of the motor currents. Thus the timing, magnitude, and direction of pressure pulses and change in flow volume without pressure pulses can be independently ordered by the physician."

While the LFBP Algorithm can be easily followed electronically by a computer or a digital signal processor (DSP), it would be much too much a distraction for the physician to give his clinical instructions in terms of motor current magnitude and frequency. In our preferred embodiment, inputs from the physician can be simple commands, for example:

(i) LFBP output pressure pulses, magnitude, duration.
(ii) gradual change in blood flow volume.
(iii) combination of (i) and (ii).
(iv) time sequences of the above inputs.
(v) if A, then B We refer to the above commands (i) through (v) as prototype commands. Each of these has one or more assignable parameters. For instance: (i) may have parameters on the exact times for each pulse to occur, and the magnitude and duration of each. (ii) may have a parameter on the amount of change, or the final value of the desired flow volume, etc. (v) represents a conditional occurrence in which A defines a condition for the event B to occur. There can be associated parameters on both A and B. For instance, if A exceeds a given threshold, B is to occur with an assigned magnitude. For each prototype command, there can be default values for the parameters. The default values are selected by the physician.

In our preferred arrangement, FIG. 2 illustrates a Digital Signal Processor based device for conversion of the prototype commands to the LFBP electrical motor currents which are specifically constituted for carrying out these commands. A Digital Signal Processor, or DSP for short, is a specialized micro-computer whose architecture is optimized for executing arithmetic instructions.[2] The DSPs, which currently run at 300 mega Hz, can execute multiplication in one clock cycle. Furthermore, the DSP's are software programmable. To follow the LFBP Algorithm in well designed steps is no problem. Referring to FIG. 2, DSP 11 has two major components: a Programming and Arithmetic Logic (PAL) Unit 12 and a memory unit 13. Both the physician's prototype command set 14 and the LFBP algorithm 15 are placed in the memory unit. With the physician's input, the selected prototype command 16 is placed in a memory slot 17 which is especially provided for the prototype command being executed. The PAL Unit 12 then converts the entry in memory slot 17 into LFBP currents 18 with specified amplitudes and frequencies as functions of time.

The AUTOPRO 20 is to take care of the patient in the physician's absence. An AUTOPRO program starts with the physician's command If A, then B where A is a threshold condition on the clinical signal set 19 and B can be a prototype command 21 on the VAD(s) and/or a command 9 on the AP pace rate and/or intensity.

The physician composes the AUTOPRO program by selecting A and B or a time sequence of A and B.

With DSP's high speed, the conversion can be completed within a few millionth of a second, which is the equivalence of instantaneous in human time scale.

Figure 3:
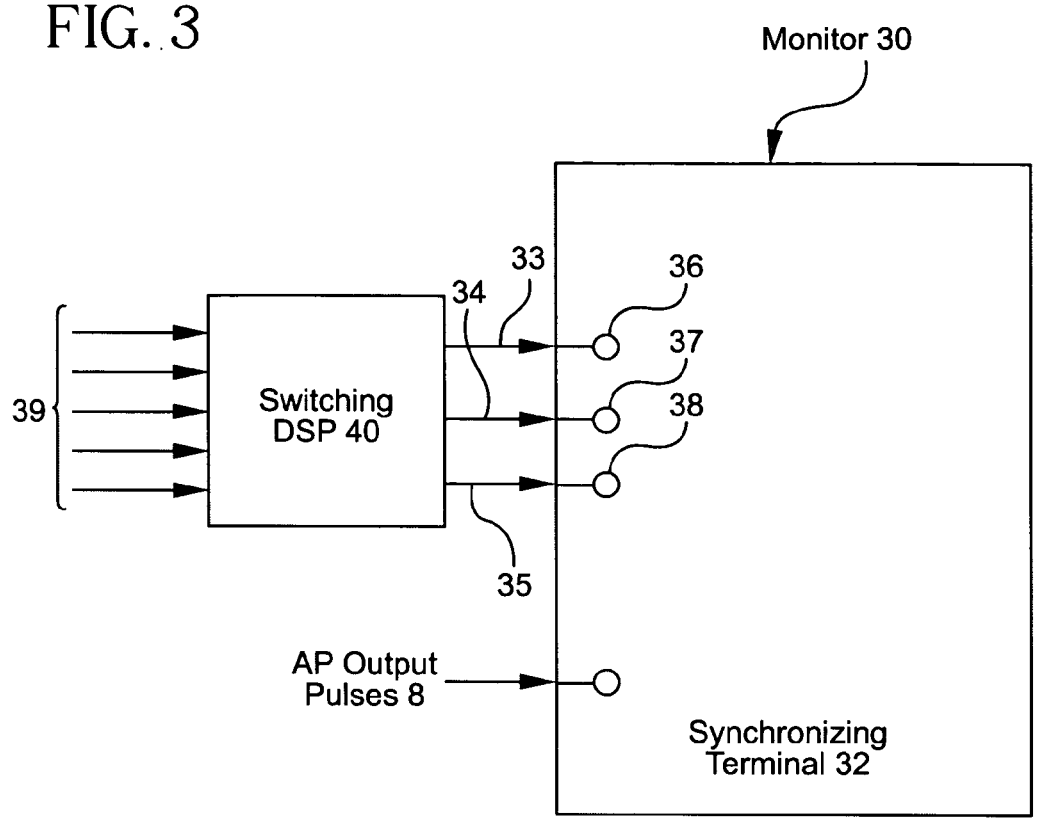
FIG. 3. illustrates the synchro-cardiac-graph (SCG) arrangement.

FIG. 3 illustrates an SCG arrangement. The output 8 from AP 7 is also connected to the horizontal sweep voltage synchronizing input terminal 32 of monitor 30. Selected clinical signal voltages 33, 34, and 35 are connected to the vertical input terminals 36, 37, and 38 of monitor 30. Each clinical signal voltage is the sum of two components:

(i) the component resulting from heart's response to each AP pulse, and
(ii) the component resulting from other physiological factors.

Since only the component (i) repeats after each AP pulse, component (i) is brightened by repetition. In contrast, component (ii) becomes a weak random blur. Thus SCG illustrates to the physician only the heart's responses to AP 8 pulses.

In general, there can be many pertinent clinical signals 39, and viewing all these signals simultaneously can be confusing. The switching DSP 40 offers the physician a way of viewing only a few selected signals such as 33, 34, and 35 at a time.

The DSP 40 can also be used for other meaningful computations: For instance, the heart's output blood volume after each AP pulse, and the heart's output blood volume per minute, etc.

Figure 4:
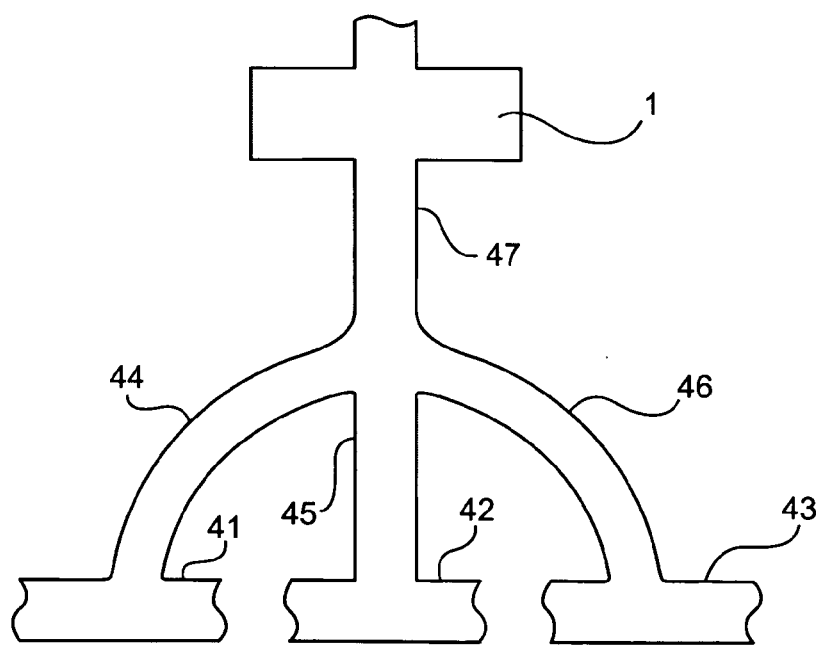
FIG. 4. illustrates multiple tapping of blood vessels for the input end of a RVAD.

FIG. 4 illustrates a distributed blood vessel tapping system. Because of the large volume of blood being pumped by the VADs, a single tapping may cause too much disturbance in the blood vessel at the point being tapped. FIG. 4 illustrates an alternative arrangement for the input line 2 of RVAD 1 in FIG. 1. Instead of tapping at one point on the vein, a plural number of taps 41, 42, and 43 are made with cannulae 44, 45, and 46 respectively which converge to a single large cannula, 47, before entering to the RVAD. Cannulae are specially designed blood conduits, which can be bent and also have the capability of standing up to external pressure or internal suction. If necessary, similar distributed arrangements can also be made for other VAD input output conduits 3, 5, and 6 of FIG. 1.

Figure 5:
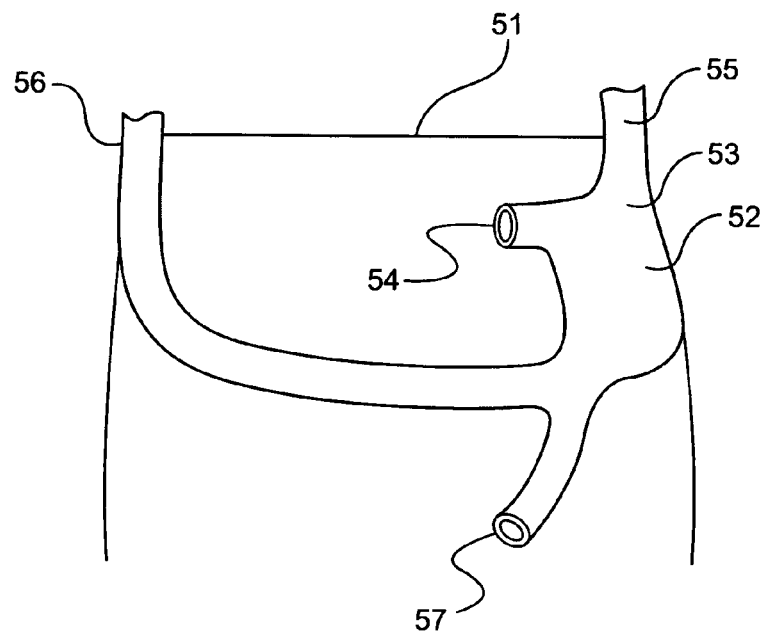
FIG. 5. illustrates the placement of a LVAD beneath the diaphragm and the LVAD's main blood conduits.

FIG. 5 illustrates the placement of a LVAD 52 below the diaphragm 51. The output end 53 of 52 is branched into two blood conduits: a lower main outlet 54, which supplies the arteries below the diaphragm 51, and an upper main outlet which is connected to a cannula 55 The cannula 55 penetrates the diaphragm 51 to supply arteries above 51. The blood inlet of LVAD 52 is supplied by a cannula 56 and a lower main inlet 57. The cannula 56 collects blood from veins above the diaphragm 51, and the main inlet 57 collects blood from veins below 51. All the blood collected by 56 and 57 goes into the inlet end of LVAD 52.

Figure 6:
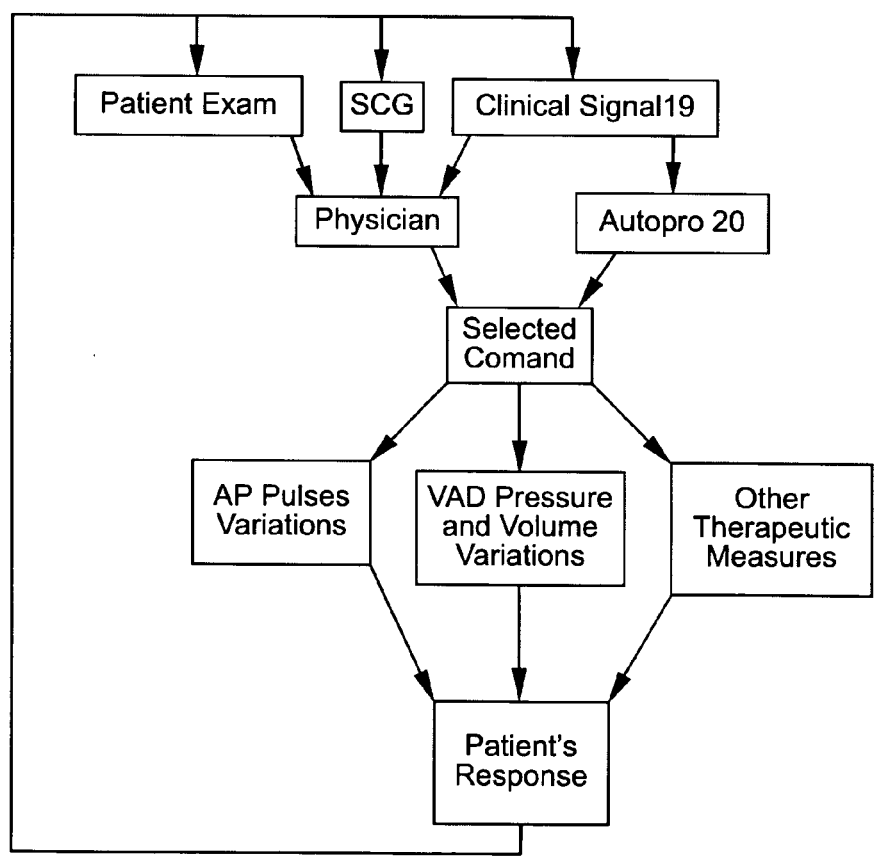
FIG. 6. illustrates the operational links and feedback paths in the curing of a patient.

FIG. 6 is an operational diagram illustrating two modes of operation:

(i) in the presence of a physician,
(ii) not in the presence of a physician.

In Mode(i) operation, the physician derives his inputs from three sources: the Synchro-Cardiac Graph of FIG. 3, slow varying clinical signals or data, and the physician's direct examination of the patient. From all these information, the physician decides on a therapeutic course of action which can include a prototype command, an AP instruction, and possible also some other means. The prototype command is then placed in memory slot 17 to be carried out through time varying LFBP motor currents 18.

However, in most of the time the patient is not with the physician, and the AUTOPRO is a sequential set of prototype instructions selected in advance by the physician. It starts with the If A, then B instruction, where A is a condition on the clinical signal 19, and B is the physician selected course of action, including prototype command 21, which is then placed in slot 17 for execution.

FIG. 6 also illustrates the signal feed backs in a curing process, the physician derives his information about the patient from three sources: direct examination of the patient, the SCG, and other slow-varying clinical signals. Based on the total information, the physician selects a prototype command. This selection is made easier by the ISC which sets up the prototype commands. The ISC also helps in the conversion of the selected command into VAD motor electrical currents for its execution. In the mean time, the physician also sends controlling radio signal to the AP. Both the changes in AP output and in VAD output will have an effect on the patient.

In its turn, the patient's response will have an effect on the outcome of the physician's observation or examination of the patient, on the SCG, and also on the clinical signals. In the absence of the physician, the AUTOPRO puts out a selected command, which has the same effect as a physician selected command in its execution, and also an AP controlling radio signal. In its turn, the patient's response will have an effect on the clinical signals, which in turn affects the AUTOPRO outputs.

In our preferred arrangement, linear flow blood pumps (LFBPs) are used for both the VADs. By varying the LVAD electrical motor current magnitude and frequency as a function of time, the pressure pulses and blood flow volume at the LVAD output can be independently controlled. Only the flow volume is controlled for the RVAD. Since its only function is to provide adequate blood flow through the pulmonary circuit such that the red blood cells flowing into the LVAD and left vertricle carry sufficient oxygen Having described my invention in full, I respectfully submit that:

1. Other types of VAD can also be used with the present invention with their corresponding set of prototype commands. Thus, using other types of VAD does not constitute a new different invention.
2. General purpose microprocessors or computers can be used instead of the DSPs. It is a designer's choice, and does not constitute a new and different invention.
3. In our preferred embodiment, magnetic induction means are used for transference of signal, information, and power across the skin without puncturing the skin. These devices and methods are well known to persons skilled in the art, and will not be described here.

The invention claimed is:

1. A ventricular assist device for use by a physician for treating a patient with a diseased heart, the device comprising:
    at least one linear flow blood pump for fluid connection between an artery and a vein of the patient, said linear flow blood pump having an electronic receiving means for receiving an operating motor current;
    a pacemaker implantable in a patient for sending electrical pulses to the patient's heart;
    a monitor suitably fixable in or on the patient for measuring clinical signals from the heart in response to said electrical pulses sent by said pacemaker;
    at least one attachment including a magnetic induction means for measuring a clinical signal from at least one other organ of the patient across the skin of the patient; and
    a control means in electrical communication with said linear flow blood pump, said pacemaker and said monitor and including an input means for entering a command, said control means simultaneously controlling said operating motor current of said linear flow blood pump and at least one of a pulse rate and voltage of said electrical pulses sent by said pacemaker based on said entered command and said clinical signals measured by said monitor.

2. A ventricular assist device as defined in claim 1, wherein said operating motor current of said linear flow blood pump controls a blood output pressure and volume of said pump.

3. A ventricular assist device as defined in claim 1, wherein said control means is pre-programmed with a prototype command, said control means controlling said linear flow blood pump and said pacemaker based additionally on said prototype command.

4. A ventricular assist device as defined in claim 1, comprising two linear flow blood pumps, wherein said control means controls said two pumps independently.

5. A ventricular assist device as defined in claim 1, wherein said control means controls said blood output pressure and volume of said linear flow blood pump by varying the magnitude and frequency of electrical motor currents of said pump.

6. A ventricular assist device as defined in claim 1, wherein said monitor includes a magnetic induction means for measuring said clinical signals from the heart across the skin of the patient.

7. A ventricular assist device as defined in claim 1, wherein said control means transmits a radio signal to said pacemaker for controlling said pulse rate and voltage of said pacemaker.

8. A ventricular assist device as defined in claim 1, wherein said control means comprises a digital signal processor.

9. A ventricular assist device as defined in claim 8, wherein said digital signal processor comprises a programming and arithmetic logic (PAL) unit and a memory unit.

10. A method for restoring a damaged heart in a living being comprising the steps of:
    sending electrical pulses to the heart via a pacemaker implanted within the living being;
    measuring clinical signals from the heart in response to said electrical pulses sent by said pacemaker;
    measuring a clinical signal from at least one other organ of the living being across the skin of the living being with a magnetic induction means;
    sending said clinical signals from the heart to a control means;
    receiving a command into said control means;
    controlling a blood output pressure and volume of a linear flow blood pump implanted in the living being with said control means based on said entered command and said measured clinical signals from the heart; and controlling at least one of a pulse rate and voltage of said electrical pulses sent by said pacemaker with said control means based on said entered command and said measured clinical signals from the heart.

11. A method as defined in claim 10, further comprising the step of pre-programming said control means with a prototype command, wherein said control means controls said linear flow blood pump and said pacemaker based additionally on said prototype command.

12. A method as defined in claim 10, wherein said control means controls two linear flow blood pumps independently.

13. A method as defined in claim 10, wherein said control means controls said blood output pressure and volume of said linear flow blood pump by varying the magnitude and frequency of electrical motor currents of said pump.

14. A method as defined in claim 10, wherein said clinical signals from the heart are measured across the skin of the living being with a magnetic induction means.

15. A method as defined in claim 10, wherein said control means transmits a radio signal to said pacemaker for controlling said pulse rate and voltage of said pacemaker.

16. A ventricular assist device as defined in claim 10, wherein said control means comprises a digital signal processor.

17. A method as defined in claim 16, wherein said digital signal processor comprises a programming and arithmetic logic (PAL) unit and a memory unit.

* * * * *